United States Patent
Jung

(10) Patent No.: US 11,033,591 B2
(45) Date of Patent: Jun. 15, 2021

(54) ANTIBACTERIAL ESSENTIAL OIL

(71) Applicant: Jong Moon Jung, Seoul (KR)

(72) Inventor: Jong Moon Jung, Seoul (KR)

( * ) Notice: Subject to any disclaimer, the term of this patent is extended or adjusted under 35 U.S.C. 154(b) by 0 days.

(21) Appl. No.: 16/780,660

(22) Filed: Feb. 3, 2020

(65) Prior Publication Data

US 2020/0171111 A1 Jun. 4, 2020

Related U.S. Application Data

(63) Continuation of application No. 15/936,599, filed on Mar. 27, 2018, now abandoned.

(30) Foreign Application Priority Data

Apr. 3, 2017 (KR) ........................ 10-2017-0042925

(51) Int. Cl.
| | | |
|---|---|---|
| *A61K 36/14* | (2006.01) | |
| *A61K 36/21* | (2006.01) | |
| *A61K 36/25* | (2006.01) | |
| *A61K 36/28* | (2006.01) | |
| *A61K 36/484* | (2006.01) | |
| *A61K 36/65* | (2006.01) | |
| *A61K 36/78* | (2006.01) | |
| *A61K 36/82* | (2006.01) | |
| *A61K 36/835* | (2006.01) | |
| *A61P 31/04* | (2006.01) | |
| *A61K 36/725* | (2006.01) | |
| *C11B 9/02* | (2006.01) | |

(52) U.S. Cl.
CPC ............. *A61K 36/14* (2013.01); *A61K 36/21* (2013.01); *A61K 36/25* (2013.01); *A61K 36/28* (2013.01); *A61K 36/484* (2013.01); *A61K 36/65* (2013.01); *A61K 36/725* (2013.01); *A61K 36/78* (2013.01); *A61K 36/82* (2013.01); *A61K 36/835* (2013.01); *A61P 31/04* (2018.01); *A61K 2236/331* (2013.01); *C11B 9/027* (2013.01)

(58) Field of Classification Search
CPC .... A61K 2300/00; A61K 36/14; A61K 36/21; A61K 36/25; A61K 36/28; A61K 36/484; A61K 36/65; A61K 36/725; A61K 36/78; A61K 36/82; A61K 36/835; A61K 2236/331; A61P 31/04; C11B 9/027
See application file for complete search history.

(56) References Cited

FOREIGN PATENT DOCUMENTS

| KR | 10-2014-0132243 A | 11/2014 |
|---|---|---|
| KR | 20140132243 A * | 11/2014 |

* cited by examiner

*Primary Examiner* — Aaron J Kosar
(74) *Attorney, Agent, or Firm* — Novick, Kim & Lee, PLLC; Jae Youn Kim

(57) ABSTRACT

An antibacterial essential oil includes 100 parts by weight of a *Juniperus chinensis* extract, 30 to 70 parts by weight of an *Aquilaria agallocha* extract, 30 to 70 parts by weight of camellia oil, and 10 to 40 parts by weight of a *Dendropanax morbifera* extract. Additionally, the antibacterial essential oil includes 10 to 40 parts by weight of a *Portulaca oleracea* extract, and 10 to 40 parts by weight of a *Houttuynia cordata* extract, 10 to 40 parts by weight of a Salicornict herhacea extract, and 10 to 40 parts by weight of a licorice extract. Further, the antibacterial essential oil includes 10 to 40 parts by weight of an *Arctium* lcwixt tea extract, 10 to 40 parts by weight of a jujube extract, 10 to 40 parts by weight of a *Paeonict japonica* extract, and 10 to 40 parts by weight of a *Chamaecyparis obtuse* extract.

7 Claims, No Drawings

ANTIBACTERIAL ESSENTIAL OIL

CROSS-REFERENCE TO RELATED APPLICATIONS

This is a continuation application of U.S. 15/936,599, filed Mar. 27, 2018, which claims priority from Korean Patent Application No. 10-2017-0042925 filed Apr. 03, 2017, which is incorporated herein by reference in its entirety.

BACKGROUND OF THE INVENTION

Field of the Invention

The present invention relates to an antibacterial essential oil, and more particularly to an antibacterial essential oil comprising a mixture of camellia oil and simple volatile aromatic compounds extracted from *Juniperus chinensis, Aquilaria agallocha, Dendropanax morbifera, Portulaca oleracea* and/or the like.

Description of the Prior Art

Essential oils are aromatic volatile organic compounds including alcohols, aldehydes, esters, ketones, oxides and the like, and are obtained from plants. According to parts from which they are obtained, these essential oils are mainly classified into those obtained from leaves ( eucalyptus and peppermint), those obtained from flowers (lavender and rosemary), those obtained from branches (juniper), those obtained from stems (sandalwood), those obtained from roots (vetiver and calamus), and the like.

In particular, aromatic essential oils contain chemicals and hormones extracted from the specific parts (root, flower, leaf, stem, fruit, etc.) of fragrant plants useful for health, that is, herbal plants. Just as various chemicals and hormones are indispensable to the human body, it can be said that the life force of plants also originates therefrom. About 300 or more kinds of oils may be used in the human body, and among them, about 60 kinds of oils are currently used in the human body.

Meanwhile, the essential oils have anti-infectious activity, antihistamine activity, antiallergic activity and the like, and exhibit unique therapeutic effects according to the composition thereof. For example, when the essential oils contain a large amount of ketone, they have an excellent wound healing effect, and when the essential oils contain a large amount of alcohol, they have an excellent antibacterial effect.

Methods of applying such essential oils to the body include a method of applying the essential oil directly to the skin, a method of spraying the essential oil to the skin, and a method of intranasally inhaling the essential oil. Among these methods, the transdermal method is most frequently used. The essential oil that passed through the skin is absorbed into capillary blood vessels and reaches the systemic circulation.

Methods that are used to apply such essential oils, particularly aromatic essential oils, include fragrance diffusion employing a lamp or a humidifier, steam (moisture) inhalation, dry inhalation, wet compress, bath, massage, spraying, gaggling and the like.

SUMMARY OF THE INVENTION

The present invention has been made in order to overcome the above-described problems, and is intended to provide an antibacterial essential oil comprising a mixture of camellia oil and simple volatile aromatic compounds extracted from *Juniperus chinensis, Aquilaria agallocha, Dendropanax morbifera, Portulaca oleracea* and the like.

The present invention provides an antibacterial essential oil comprising: 100 parts by weight of a *Juniperus chinensis* extract; 30 to 70 parts by weight of an *Aquilaria agallocha* extract; 30 to 70 parts by weight of camellia oil; 10 to 40 parts by weight of a *Dendropanax morbifera* extract; 10 to 40 parts by weight of a *Portulaca oleracea* extract; 10 to 40 parts by weight of a *Houttuynia cordata* extract; 10 to 40 parts by weight of a *Salicornia herbacea* extract; 10 to 40 parts by weight of a licorice extract; 10 to 40 parts by weight of an *Arctium lappa* tea extract; 10 to 40 parts by weight of a jujube extract; 10 to 40 parts by weight of a *Paeonia japonica* extract; and 10 to 40 parts by weight of a *Chamaecyparis obtuse* extract.

DETAILED DESCRIPTION OF THE INVENTION

Hereinafter, the present invention will be described in detail.

The terminology used herein is for the purpose of describing particular embodiments only and is not intended to limit the scope of the invention. As used herein, the singular forms are intended to include the plural forms as well, unless the context clearly indicates otherwise. It will be further understood that the terms "comprises" and/or "comprising," when used in this specification, specify the presence of stated shapes, numbers, steps, operations, elements and/or components, but do not preclude the presence or addition of one or more other shapes, numbers, steps, operations, elements and/or components.

The present invention provides an antibacterial essential oil comprising: 100 parts by weight of a *Juniperus chinensis* extract; 30 to 70 parts by weight of an *Aquilaria agallocha* extract; 30 to 70 parts by weight of camellia oil; 10 to 40 parts by weight of a *Dendropanax morbifera* extract; 10 to 40 parts by weight of a *Portulaca oleracea* extract; 10 to 40 parts by weight of a *Houttuynia cordata* extract; 10 to 40 parts by weight of a *Salicornia herbacea* extract; 10 to 40 parts by weight of a licorice extract; 10 to 40 parts by weight of an *Arctium lappa* tea extract; 10 to 40 parts by weight of a jujube extract; 10 to 40 parts by weight of a *Paeonia japonica* extract; and 10 to 40 parts by weight of a *Chamaecyparis obtuse* extract.

The antibacterial essential oil according to the present invention is prepared by aging and blending plant extracts safe for the human body. Thus, it causes no skin irritation, and is safe even when being used for a long period of time. In addition, it may be formulated as skin lotion or essence which may be provided in a glass bottle or a general cosmetic bottle so as to be easily used by spraying. To this end, the antibacterial essential oil according to the present invention may be provided in the form of any conventional antibacterial essential oil known in the art.

In particular, the antibacterial essential oil according to the present invention is preferably formulated as liquid products such as skin softener, essence and/or skin lotion products.

Meanwhile, the extracts according to the present invention, particularly extracts of plants, including *Juniperus chinensis, Aquilaria agallocha, Dendropanax morbifera, Portulaca oleracea, Houttuynia cordata, Salicornia herbacea*, licorice, *Arctium lappa* tea, jujube, *Paeonia japonica*, and *Chamaecyparis obtuse*, may be prepared by any extraction method known in the art. Preferably, the extracts may be prepared by extracting plants, for example, *Juniperus chinensis, Aquilaria agallocha, Dendropanax morbifera, Portulaca oleracea, Houttuynia cordata, Salicornia herbacea,* licorice, *Arctium lappa* tea, jujube, *Paeonia japonica* and/or *Chamaecyparis obtuse*, by steam distillation at a temperature ranging from 65 to 75° C. for 45 to 50 hours.

The *Juniperus chinensis* extract according to the present invention is an extract obtained from *Juniperus chinensis*, preferably the leaf and/or stem of *Juniperus chinensis*.

In this regard, *Juniperus chinensis* is known as a fragrant tree, acts to cleanse the mind and destroy the unclean thing, and has antibacterial activity. Thus, it has been widely used for skin care and cleansing by the women of the King's court.

In particular, the *Juniperus chinensis* has been widely known to have an air cleaning effect, and studies on the *Juniperus chinensis* have been actively conducted to use the *Juniperus chinensis* against various stress-induced skin diseases and for scale care. Furthermore, studies on the *Juniperus chinensis* indicated that the *Juniperus chinensis* showed the best antibacterial effect against *Propionibacterium acnes* which is a representative acne-causing bacterium [see Korean journal of aesthetics and cosmetics society, Vol. 2 No. 2 (Antibacterial, antioxidant and keratinocyte-protecting effects of *Juniperus chinensis* extract, the Department of Biotechnology, Chosun University, and others).

The contents of components other than the *Juniperus chinensis* extract in the antibacterial essential oil according to the present invention are based on 100 parts by weight of the *Juniperus chinensis* extract.

The *Aquilaria agallocha* extract according to the present invention is an extract obtained from *Aquilaria agallocha* which is conventionally used in the art, particularly Vietnamese *Aquilaria agallocha* (*Aquilaria crassna*). The *Aquilaria agallocha* extract is preferably used in an amount of 30 to 70 parts by weight based on 100 parts by weight of the *Juniperus chinensis* extract.

In this regard, the *Aquilaria agallocha* extract comprises simple volatile aromatic compounds which are the major components of *Aquilaria crassna* and which are effective for acne, stress-induced skin diseases, mite bites, insect bites, mosquito bites, mosquito repellent, skin aging caused by environmental pollution or the like, and atopic symptoms.

In addition, the *Aquilaria agallocha* extract has flower scent, soft herbal fragrance, and pleasant fresh fragrance.

The camellia oil according to the present invention is an oil extracted from the seed, leaf, bud and/or fruit of Camellia japonica, and contains a large amount of oleic acid which has a good skin moisturizing effect and a skin soothing effect and which is effective against atopic or allergic skin conditions. In addition, it is rich in gamma-linolenic acid which is effective in preventing skin dryness and alleviating itching.

The camellia oil is preferably used in an amount of 30 to 70 parts by weight based on 100 parts by weight of the *Juniperus chinensis* extract, but is not particularly limited thereto.

The *Dendropanax morbifera* extract according to the present invention is an extract obtained from *Dendropanax morbifera* which is a dicotyledonous evergreen tree belonging to the family Araliaceae of the order Umbelliflorae. It has antioxidant and antimicrobial or antibacterial activities, and contains a large amount of sesquiterpene which has the effect of stabilizing mind and body.

The *Dendropanax morbifera* extract is preferably used in an amount of 10 to 40 parts by weight based on 100 parts by weight of the *Juniperus chinensis* extract.

The *Portulaca oleracea* extract according to the present invention is an extract obtained from *Portulaca oleracea*, particularly the leaf and the like of *Portulaca oleracea*. It acts to alleviate skin irritation and allergic responses, and has pharmacological effects such as antibacterial and anti-inflammatory effects. Thus, it is used mainly in acne care products, cosmetics for sensitive skin, and the like.

The *Portulaca oleracea* extract is preferably used in an amount of 10 to 40 parts by weight based on 100 parts by weight of the *Juniperus chinensis* extract, but is not particularly limited thereto.

The *Houttuynia cordata* extract according to the present invention is an extract obtained from *Houttuynia cordata* which is a dicotyledonous perennial plant belonging to the family Saururaceae of the order Piperales. It is effective in treating skin inflammation, atopic diseases and the like.

The *Houttuynia cordata* extract is preferably used in an amount of 10 to 40 parts by weight based on 100 parts by weight of the *Juniperus chinensis* extract.

The *Salicornia herbacea* extract according to the present invention is an extract obtained from *Salicornia herbacea* which is a dicotyledonous annual plant belonging to the family Chenopodiaceae of the order Centrospermales. It is good for skin beauty so that it can call an eating cosmetic. In addition, it is rich in minerals and vitamins, and thus has an excellent effect on fatigue recovery.

The *Salicornia herbacea* extract is preferably used in an amount of 10 to 40 parts by weight based on 100 parts by weight of the *Juniperus chinensis* extract.

The licorice extract according to the present invention is an extract obtained from licorice which is a dicotyledonous perennial plant belonging to the family Fabaceae of the order Rosales. It has good detoxifying and anti-inflammatory effects, and is effective in alleviating skin diseases such as acne, atopy, eczema, urticaria and the like.

The licorice extract is preferably used in an amount of 10 to 40 parts by weight based on 100 parts by weight of the *Juniperus chinensis* extract.

The *Arctium lappa* tea extract according to the present invention is an extract obtained from a tea made of an *Arctium lappa* seed obtained by drying the ripe seed of *Arctium lappa* belonging to the family Asteraceae. It has a blood pressure regulating effect, an anticancer effect, a detoxifying effect, a bad breath removing effect and a blood glucose lowering effect, and is effective in reducing freckles, wrinkles and the like.

The *Arctium lappa* tea extract is preferably used in an amount of 10 to 40 parts by weight based on 100 parts by weight of the *Juniperus chinensis* extract.

The jujube extract according to the present invention is an extract obtained from the fruit of jujube. It gives conditioning to the skin to help make the skin vital, and is effective in moisturizing the skin and keeping the skin healthy.

The jujube extract is preferably used in an amount of 10 to 40 parts by weight based on 100 parts by weight of the *Juniperus chinensis* extract.

The *Paeonia japonica* extract according to the present invention is an extract obtained from *Paeonia japonica* which is a dicotyledonous perennial plant belonging to the family Ranunculaceae of the order Ranunculales. It shows an anti-aging effect and is effective in preventing dermatitis and inhibiting melanin formation.

The *Paeonia japonica* extract is preferably used in an amount of 10 to 40 parts by weight based on 100 parts by weight of the *Juniperus chinensis* extract.

The *Chamaecyparis obtuse* extract according to the present invention is an extract obtained from *Chamaecyparis*

*obtuse* which is an evergreen tree belonging to the family Cupressaceae of the order Coniferales of Pinophyta. It contains a large amount of the natural antibacterial compound phytoncide having an excellent sterilizing effect, and has strong water resistance so that when it contacts water, its original fragrance can spread deeply to eliminate other odors.

The *Chamaecyparis obtuse* extract is preferably used in an amount of 10 to 40 parts by weight based on 100 parts by weight of the *Juniperus chinensis* extract.

In a certain embodiment, the antibacterial essential oil according to the present invention may further comprise, based on 100 parts by weight of the *Juniperus chinensis* extract, 1 to 10 parts by weight of perfume in order to improve the user's feeling by adding fragrance.

Preferred examples of perfume that may be used in the present invention include herbs such as lavender, rosemary, oregano, bergamot, yarrow, basil, mint, sage or lemon balm, jasmine, borage, anika, spatium, Clary sage, peppermint and the like.

In another certain embodiment, the antibacterial essential oil according to the present invention may further comprise, based on 100 parts by weight of the *Juniperus chinensis* extract, 0.01 to 3 parts by weight of an antioxidant in order to prevent oxidation of the antibacterial essential oil.

Preferred examples of an antioxidant that may be used in the present invention include amine-based antioxidants, biophenol-based antioxidants, monophenol-based antioxidants, and sulfur-based antioxidants. More preferably, the antioxidant is 2,2-methylenebis(4-methyl-6-t-butylphenol), 2,6-di-t-butyl-4-methylphenol, or a mixture thereof.

In still another certain embodiment, the antibacterial essential oil according to the present invention may further comprise salicylic acid in order to prevent bacteria or the like from occurring in the antibacterial essential oil. The salicylic acid is preferably used in an amount of 0.01 to 2 parts by weight based on 100 parts by weight of the *Juniperus chinensis* extract.

In still another certain embodiment, the antibacterial essential oil according to the present invention may further comprise stearic acid in order to form a thin protective layer when the oil is applied to the skin, thereby relieving external physical impact and preventing the penetration of toxic substances and also preventing the skin temperature from being reduced. The stearic acid is preferably used in an amount of 0.01 to 2 parts by weight based on 100 parts by weight of the *Juniperus chinensis* extract.

In still another certain embodiment, the antibacterial essential oil according to the present invention may further comprise para-aminobenzoic acid in order to absorb UV rays. The para-aminobenzoic acid is preferably used in an amount of 0.01 to 2 parts by weight based on 100 parts by weight of the *Juniperus chinensis* extract.

In still another certain embodiment, the antibacterial essential oil according to the present invention may further comprise a *Cotoneaster horizontalis Decne* extract in order to increase the antioxidant and anti-inflammatory effects of the essential oil. In this regard, the *Cotoneaster horizontalis Decne* belongs to the genus Cotoneaster of the family Rosaceae, and is distributed mainly in temperate regions, including North America and Europe. The *Cotoneaster horizontalis Decne* extract is prepared according to the same extraction method as that used for each extract of the present invention, and is preferably used in an amount of 5 to 30 parts by weight based on 100 parts by weight of the *Juniperus chinensis* extract.

In still another certain embodiment, the antibacterial essential oil according to the present invention may further comprise a *Martensia bibarii* extract in order to prevent autoimmune diseases or inflammatory diseases. In this regard, *Martensia bibarii* is a red algae belonging to the order Ceramiales, and is distributed in the southern coast of Korea and in the sea area of Jeju Island, Korea. The *Martensia bibarii* extract is prepared according to the same extraction method as that used for each extract of the present invention, and is preferably used in an amount of 5 to 30 parts by weight based on 100 parts by weight of the *Juniperus chinensis* extract.

In still another certain embodiment, the antibacterial essential oil according to the present invention may further comprise, based on 100 parts by weight of the *Juniperus chinensis* extract, 3 to 20 parts by weight of hyaluronic acid in order to improve the skin moisturizing effect of the essential oil.

In this regard, the hyaluronic acid is a biomaterial having a very excellent skin-moisturizing effect.

In still another certain embodiment, the antibacterial essential oil according to the present invention may further comprise, based on 100 parts by weight of the *Juniperus chinensis* extract, 1 to 10 parts by weight of arbutin in order to improve the whitening effect of the essential oil.

In this regard, the arbutin is a substance which is contained in bearberry trees in large amounts, has a good whitening effect, and also has a chemical structure similar to that of hydroquinone acting to inhibit melanin production.

The antibacterial essential oil according to the present invention may be formulated as skin lotion or essence which may be provided in a glass bottle or a general cosmetic bottle so as to be easily used by spraying.

For use, the antibacterial essential oil according to the present invention may be diluted with a suitable amount of purified water, particularly distilled water, at a weight ratio of 1:9 to 9:1 (essential oil:distilled water), and then aged at a temperature ranging from 20° C. to 24° C. for 6 to 10 days, preferably one week.

Furthermore, the antibacterial essential oil according to the present invention may be used for adolescent acne and rough skin and to prevent skin aging, alleviate atopy and give a sense of freshness.

In addition, it may act to reduce skin heat caused by anger or stress, may alleviate the pain of bug bites (mite or mosquito bites, etc.) and help repel bugs, and is effective in alleviating rough skin and making the skin shiny through its antibacterial and antioxidant effects.

Hereinafter, the present invention will be described in detail with reference to examples. It is to be understood, however, that these examples are for illustrative purposes only and are not intended to limit the scope of the present invention.

Example 1: Extract Preparation

A *Juniperus chinensis*, *Aquilaria agallocha*, *Dendropanax morbifera*, *Portulaca oleracea*, *Houttuynia cordata*, *Salicornia herbacea*, licorice, *Arctium lappa* tea, jujube, *Paeonia japonica* or *Chamaecyparis obtuse* extract was prepared as follows.

First, the plant to be extracted, that is, *Juniperus chinensis*, *Aquilaria agallocha*, *Dendropanax morbifera*, *Portulaca oleracea*, *Houttuynia cordata*, *Salicornia herbacea*, licorice, *Arctium lappa* tea, jujube, *Paeonia japonica* or *Chamaecyparis obtuse*, was washed clean.

Here, for the *Juniperus chinensis*, the leaf or stem thereof was used, and for the *Portulaca oleracea*, the leaf thereof was used.

Next, the plant to be extracted was placed I a container to be supplied with steam, and was then subjected to a steam distillation process in which steam was continuously supplied to the plant at about 70° C. for about 48 hours, thereby obtaining an extract from the plant.

Next, the obtained extract was cooled, thereby preparing each extract.

Example 2

100 g of the *Juniperus chinensis* extract, 50 g of the *Aquilaria agallocha* extract, 50 g of camellia oil, 25 g of the *Dendropanax morbifera* extract, 25 g of the *Portulaca oleracea* extract, 25 g of the *Houttuynia cordata* extract, 25 g of the *Salicornia herbacea* extract, 25 g of the licorice extract, 25 g of the *Arctium lappa* tea extract, 25 of the jujube extract, 25 g of the *Paeonia japonica* extract, and 25 g of the *Chamaecyparis obtuse* extract, which were obtained according to the method described in Example 1, were mixed with one another, thereby preparing an antibacterial essential oil.

Example 3

This Example was performed in the same manner as described in Example 2, except that 5 g of lavender oil was further added.

Example 4

This Example was performed in the same manner as described in Example 2, except that 1.5 g of 2,2-methylenebis(4-methyl-6-t-butylphenol) was further added.

Example 5

This Example was performed in the same manner as described in Example 2, except that 1 g of salicylic acid was further added.

Example 6

This Example was performed in the same manner as described in Example 2, except that 1 g of stearic acid was further added.

Example 7

This Example was performed in the same manner as described in Example 2, except that 1.5 g of para-aminobenzoic acid was further added.

Example 8

This Example was performed in the same manner as described in Example 2, except that 10 g of a *Cotoneaster horizontalis Decne* extract prepared by the same extraction method as described in Example 1 was further added.

Example 9

This Example was performed in the same manner as described in Example 2, except that 10 g of a *Martensia bibarii* extract prepared by the same extraction method as described in Example 1 was further added.

Example 10

This Example was performed in the same manner as described in Example 2, except that 10 g of hyaluronic acid was further added.

Example 11

This Example was performed in the same manner as described in Example 2, except that 5 g of arbutin was further added.

Test

The effects (including antibacterial, antioxidant, keratinocyte protective, skin moisturizing, acne reducing, and skin cleansing effects) of the antibacterial essential oils prepared in Examples 2 to 11 were tested through use of these essential oils.

The results of the test are shown in Table 1 below.

The results in Table 1 below are the results obtained by allowing 50 male and 50 female volunteers (regardless of age) to use the essential oils and to fill in the questionnaire.

TABLE 1

| Example | Antibacterial | Antioxidant | Keratinocyte protection | Skin moisturization | Skin cleansing | Acne reduction |
| --- | --- | --- | --- | --- | --- | --- |
| 2 | Very good | Very good | Good | Good | Good | Good |
| 3 | Very good | Very good | Moderate | Good | Moderate | Good |
| 4 | Very good | Very good | Good | Good | Moderate | Good |
| 5 | Very good | Very good | Good | Good | Good | Good |
| 6 | Very good | Very good | Moderate | Good | Moderate | Good |
| 7 | Very good | Very good | Good | Good | Moderate | Good |
| 8 | Very good | Very good | Good | Good | Good | Good |
| 9 | Very good | Very good | Moderate | Good | Moderate | Good |
| 10 | Very good | Very good | Moderate | Very good | Moderate | Good |
| 11 | Very good | Very good | Moderate | Good | Moderate | Good |

As shown in Table 1 above, the antibacterial essential oils according to the present invention were moderate or higher in terms of antibacterial, antioxidant, skin moisturization, acne reduction and the like.

As described above, the antibacterial essential oil according to the present invention well combines the advantages of main materials, including *Juniperus chinensis, Aquilaria agallocha, Dendropanax morbifera, Portulaca oleracea, Houttuynia cordata, Salicornia herbacea*, licorice, *Arctium lappa* tea, jujube, *Paeonia japonica*, and *Chamaecyparis obtuse*, and emits a unique natural scent which is comfortable like wild chrysanthemum fragrance and soft like the scent of fields and mountains. Furthermore, it is harmless to the human body and has the effect of alleviating dermatitis and acne by exhibiting antibacterial activity.

In addition, the antibacterial essential oil according to the present invention is prepared by aging and blending plant extracts safe for the human body. Thus, it causes no skin irritation, is safe even when being used for a long period of time, and has the effect of alleviating itching, allergic symptoms such as skin rash, acne, or skin troubles caused by atopic skin conditions.

In addition, the antibacterial essential oil according to the present invention may be formulated as skin lotion or essence which may be provided in a glass bottle or a general cosmetic bottle so as to be easily used by spraying. Furthermore, it may be supplied at affordable prices, and thus may be used safely and conveniently by anyone regardless of gender and age.

While the present invention has been described with reference to the particular illustrative embodiments, those skilled in the art will understand that the present invention may be embodied in other specific forms without departing from the technical spirit or essential characteristics of the present invention. Therefore, the embodiments described above should be considered to be illustrative in all respects and not restrictive. Furthermore, it should be understood that all modifications or variations derived from the meanings and scope of the present invention and equivalents thereof are included in the scope of the present invention.

What is claimed is:

1. A method for preparing an antibacterial essential oil, the method comprising:
    a washing step of washing *Juniperus chinensis* leaf and stem, *Aquilaria agallocha*, *Dendropanax morbifera*, *Chamaecyparis obtusa*, *Portulaca oleracea* leaf, *Houttuynia cordata*, *Salicornia herbacea*, *Arctium lappa*, jujube, *Paeonia japonica*, *Camellia japonica* seed, leaf or bud, and licorice;
    after the washing step, a crushing step of crushing the washed *Aquilaria agallocha*, *Dendropanax morbifera* and *Chamaecyparis obtusa* into chips, and crushing the washed *Juniperus chinensis* leaf and stem, *Portulaca oleracea* leaf, *Houttuynia cordata*, *Salicornia herbacea*, *Arctium lappa*, jujube, *Paeonia japonica*, *Camellia japonica* seed, leaf or bud, and licorice into powder;
    after the crushing step, a first extraction step of placing the crushed *Aquilaria agallocha*, *Dendropanax morbifera* and *Chamaecyparis obtusa* in extraction tanks, respectively, supplying steam to the extraction tanks, and liquefying steam, discharged from the extraction tanks, in condensers, thereby preparing extracts;
    a second extraction step of placing the crushed *Juniperus chinensis* leaf and stem, *Portulaca oleracea* leaf, *Houttuynia cordata*, *Salicornia herbacea*, *Arctium lappa*, jujube, *Paeonia japonica*, and *Camellia japonica* seed, leaf or bud, and licorice in extraction tanks, respectively, infusing them by heating, and then filtering out precipitate, floating material or dregs, thereby preparing extracts;
    a mixing step of mixing the extracts prepared in the first extraction step and the second extraction step;
    a heating and filtration step of heating the extract mixture, obtained in the mixing step, in hot water, and then filtering out dregs, floating material or precipitate; and
    a dilution and aging step of diluting the extract mixture, subjected to the heating and filtration step, with distilled water, and aging the diluted extract mixture for 6 to 10 days.

2. The method of claim 1, wherein the first extraction step comprises:
    placing the *Chamaecyparis obtusa*, crushed into chips in the crushing step, in an extraction tank, supplying steam having a temperature of 75 to 110° C. to the extraction tank for 35 to 55 hours, and liquefying steam, discharged from the extraction tank, in a condenser, thereby preparing a *Chamaecyparis obtusa* extract;
    placing the *Dendropanax morbifera* chips, obtained in the crushing step, in an extraction tank, supplying steam having a temperature of 75 to 110° C. to the extraction tank for 35 to 55 hours, and liquefying steam, discharged from the extraction tank, in a condenser, thereby preparing a *Dendropanax morbifera* extract; and
    placing the *Aquilaria agallocha*, crushed into chips, in an extraction tank, supplying steam having a temperature of 75 to 110° C. to the extraction tank for 35 to 55 hours, and liquefying steam, discharged from the extraction tank, in a condenser, thereby preparing an *Aquilaria agallocha* extract.

3. The method of claim 1, wherein the second extraction step comprises:
    adding purified water to the *Juniperus chinensis* leaf and stem, crushed into powder in the crushing step, infusing the *Juniperus chinensis* leaf and stem by heating at 80 to 95° C. for 5 to 15 minutes, and then filtering out precipitate, floating material or dregs, thereby preparing a *Juniperus chinensis* extract;
    adding purified water to the jujube, crushed into powder in the crushing step, infusing the jujube by heating at 80 to 95° C. for 5 to 15 minutes, and then filtering out precipitate, floating material or dregs, thereby preparing a jujube extract;
    adding purified water to the *Portulaca oleracea* leaf, crushed into powder in the crushing step, infusing the *Portulaca oleracea* leaf by heating at 80 to 95° C. for 5 to 15 minutes, and then filtering out precipitate, floating material or dregs, thereby preparing a *Portulaca oleracea* extract;
    adding purified water to the *Houttuynia cordata* powder, infusing the *Houttuynia cordata* powder by heating at 80 to 95° C. for 5 to 15 minutes, and then filtering out precipitate, floating material or dregs, thereby preparing a *Houttuynia cordata* extract;
    adding purified water to the *Salicornia herbacea*, crushed into powder in the crushing step, infusing the *Salicornia herbacea* by heating at 80 to 95° C. for 5 to 10 minutes, and then filtering out precipitate, floating material or dregs, thereby preparing a *Salicornia herbacea* extract;
    adding purified water to the *Arctium lappa*, crushed into powder in the crushing step, infusing the *Arctium lappa* by heating at 80 to 95° C. for 3 to 10 minutes, and then filtering out precipitate, floating material or dregs, thereby preparing an *Arctium lappa* extract;
    adding purified water to the *Paeonia japonica*, crushed into powder in the crushing step, infusing the *Paeonia japonica* by heating at 80 to 95° C. for 3 to 10 minutes, and then filtering out precipitate, floating material or dregs, thereby preparing a *Paeonia japonica* extract;
    adding purified water to the *Camellia japonica* seed, leaf or bud, crushed into powder in the crushing step, infusing the *Camellia japonica* seed, leaf or bud by heating at 80 to 95° C. for 3 to 10 minutes, and then filtering out precipitate, floating material or dregs, thereby preparing a camellia oil; and adding purified water to the licorice, crushed into powder in the crushing step, infusing the licorice by heating at 80 to 95° C. for 5 to 20 minutes, and then filtering out precipitate, floating material or dregs, thereby preparing a licorice extract.

4. The method of claim 1, wherein the mixing step comprises mixing 100 parts by weight of the *Juniperus chinensis* extract, 30 to 70 parts by weight of the *Aquilaria agallocha* extract, 30 to 70 parts by weight of the camellia oil, 10 to 40 parts by weight of the *Dendropanax morbifera* extract, 10 to 40 parts by weight of the *Portulaca oleracea* extract, 10 to 40 parts by weight of the *Houttuynia cordata* extract, 10 to 40 parts by weight of the *Salicornia herbacea* extract, 10 to 40 parts by weight of the licorice extract, 10 to 40 parts by weight of the *Arctium lappa* tea extract, 10 to 40 parts by weight of the jujube extract, 10 to 40 parts by weight of the *Paeonia japonica* extract, and 10 to 40 parts by weight of the *Chamaecyparis obtusa* extract.

5. The method of claim 1, wherein the heating step comprises heating the extract mixture in hot water at 50 to 65° C. for 24 to 48 hours.

6. The method of claim 1, wherein the aging step comprises diluting the extract mixture with distilled water at a weight ratio of 1:9 to 9:1, followed by aging at a temperature of 20 to 24° C. for 6 to 10 days.

7. A method for preparing an antibacterial essential oil, the method comprising:
1) a washing step of washing *Juniperus chinensis* leaf and stem, *Aquilaria agallocha*, *Dendropanax morbifera*, *Chamaecyparis obtusa*, *Portulaca oleracea* leaf, *Houttuynia cordata*, *Salicornia herbacea*, *Arctium lappa*, jujube, *Paeonia japonica*, *Camellia japonica* seed, leaf or bud, and licorice;
2) a crushing step of crushing the washed *Aquilaria agallocha*, *Dendropanax morbifera* and *Chamaecyparis obtusa* into chips, and crushing the washed *Juniperus chinensis* leaf and stem, *Portulaca oleracea* leaf, *Houttuynia cordata*, *Salicornia herbacea*, *Arctium lappa*, jujube, *Paeonia japonica*, and *Camellia japonica* seed, leaf or bud, and licorice into powder, after completion of the washing step;
3) an extraction step comprising:
placing the *Juniperus chinensis* leaf and stem powder and distilled water in an extraction tank, infusing the *Juniperus chinensis* leaf and stem powder by heating at a temperature of 80 to 95° C. for 5 to 10 minutes, and filtering out precipitate, floating material or dregs, thereby preparing a *Juniperus chinensis* extract;
placing the *Chamaecyparis obtusa* chips in an extraction tank, supplying steam having a temperature of 75 to 110° C. to the extraction tank for 35 to 55 hours, liquefying steam, discharged from the extraction tank, in a condenser, thereby preparing a *Chamaecyparis obtusa* extract;
placing the *Dendropanax morbifera* chips in an extraction tank, supplying steam having a temperature of 75 to 110° C. to the extraction tank for 35 to 55 hours, liquefying steam, discharged from the extraction tank, in a condenser, thereby preparing a *Dendropanax morbifera* extract;
placing the *Aquilaria agallocha* chips in an extraction tank, supplying steam having a temperature of 75 to 110° C. to the extraction tank for 35 to 55 hours, liquefying steam, discharged from the extraction tank, in a condenser, thereby preparing an *Aquilaria agallocha* extract;
mixing the jujube powder with purified water, infusing the jujube powder by heating at 80 to 95° C. for 5 to 15 minutes, and filtering out precipitate, floating material or dregs, thereby preparing a jujube extract;
mixing the *Portulaca oleracea* leaf powder with purified water, infusing the *Portulaca oleracea* leaf powder by heating at 80 to 95° C. for 5 to 15 minutes, and filtering out precipitate, floating material or dregs, thereby preparing a *Portulaca oleracea* extract;
mixing the *Houttuynia cordata* powder with purified water, infusing the *Houttuynia cordata* powder by heating at 80 to 95° C. for 5 to 10 minutes, and filtering out precipitate, floating material or dregs, thereby preparing a *Houttuynia cordata* extract;
mixing the *Salicornia herbacea* powder with purified water, infusing the *Salicornia herbacea* powder by heating at 80 to 95° C. for 5 to 10 minutes, and filtering out precipitate, floating material or dregs, thereby preparing a *Salicornia herbacea* extract;
mixing the *Arctium lappa* powder with purified water, infusing the *Arctium lappa* powder by heating at 80 to 95° C. for 3 to 10 minutes, and filtering out precipitate, floating material or dregs, thereby preparing an *Arctium lappa* extract;
mixing the *Paeonia japonica* powder with purified water, infusing the *Paeonia japonica* powder by heating at 80 to 95° C. for 3 to 10 minutes, and filtering out precipitate, floating material or dregs, thereby preparing a *Paeonia japonica* extract;
mixing the *Camellia japonica* seed, leaf or bud powder with purified water, infusing the *Camellia japonica* seed, leaf or bud powder by heating at 80 to 95° C. for 3 to 10 minutes, and filtering out precipitate, floating material or dregs, thereby preparing a camellia oil; and
mixing the licorice powder with purified water, infusing the licorice powder by heating at 80 to 95° C. for 5 to 20 minutes, and filtering out precipitate, floating material or dregs, thereby preparing a licorice extract;
4) a mixing step of mixing 100 parts by weight of the *Juniperus chinensis* extract, 30 to 70 parts by weight of the *Aquilaria agallocha* extract, 30 to 70 parts by weight of the camellia oil, 10 to 40 parts by weight of the *Dendropanax morbifera* extract, 10 to 40 parts by weight of the *Portulaca oleracea* extract, 10 to 40 parts by weight of the *Houttuynia cordata* extract, 10 to 40 parts by weight of the *Salicornia herbacea* extract, 10 to 40 parts by weight of the licorice extract, 10 to 40 parts by weight of the *Arctium lappa* tea extract, 10 to 40 parts by weight of the jujube extract, 10 to 40 parts by weight of the *Paeonia japonica* extract, and 10 to 40 parts by weight of the *Chamaecyparis obtusa* extract.
5) a heating step of heating the extract mixture in hot water at 50 to 65° C. for 24 to 48 hours;
6) a second filtration step of filtering out precipitate, floating material or dregs after the heating step; and
7) an aging step of diluting the extract mixture, subjected to the second filtration step, with distilled water at a weight ratio of 1:9 to 9:1, followed by aging at a temperature of 20 to 24° C. for 6 to 10 days.

* * * * *